United States Patent [19]
Richter et al.

[11] Patent Number: 6,090,939
[45] Date of Patent: Jul. 18, 2000

[54] PROCESS FOR PREPARING POLYISOCYANATES CONTAINING IMINOOXADIAZINEDIONE GROUPS

[75] Inventors: Frank Richter, Leverkusen; Eberhard Stelter; Wilfried Litz, both of Köln; Stefan Groth, Leverkusen, all of Germany

[73] Assignee: Bayer Aktiengesellschaft, Leverkusen, Germany

[21] Appl. No.: 09/318,537

[22] Filed: May 25, 1999

[30] Foreign Application Priority Data

Jun. 2, 1998 [DE] Germany .......................... 198 24 485
Jun. 2, 1998 [DE] Germany .......................... 198 24 490

[51] Int. Cl.$^7$ ...................... C07D 273/04; C07D 251/34; C08G 18/16; C08G 18/79; C08G 18/72

[52] U.S. Cl. ................................ 544/67; 528/51; 528/67; 528/73; 528/74; 544/68; 544/193; 544/222

[58] Field of Search ................................ 528/51, 67, 73, 528/74; 544/67, 68, 193, 222

[56] References Cited

U.S. PATENT DOCUMENTS

| | | | |
|---|---|---|---|
| 4,736,008 | 4/1988 | Kouno et al. | 528/57 |
| 4,785,069 | 11/1988 | Kouno et al. | 528/51 |
| 4,937,339 | 6/1990 | Shiomura et al. | 544/193 |
| 4,992,548 | 2/1991 | Scholl et al. | 544/193 |
| 5,013,838 | 5/1991 | Scholl | 544/193 |
| 5,717,091 | 2/1998 | Richter et al. | 544/67 |
| 5,882,544 | 3/1999 | Richter et al. | 252/183.12 |
| 5,914,383 | 6/1999 | Richter et al. | 528/59 |

FOREIGN PATENT DOCUMENTS 2200823   9/1997   Canada.

OTHER PUBLICATIONS

J. Thermal Anal. 1983, pp. 215–228.

*Primary Examiner*—Rabon Sergent
*Attorney, Agent, or Firm*—Joseph C. Gil; Thomas W. Roy

[57] ABSTRACT

The present invention relates to a process for the preparation of trimerized polyisocyanates that contain at least 30 mole % of iminooxadiazinedione groups (asymmetric trimers) in the trimer mixture, by catalytically trimerizing a starting isocyanate selected from organic di- or polyisocyanates having a number average molecular weight of 140 to 600 and containing aliphatically, cycloaliphatically and/or araliphatically bound isocyanate groups in the presence of a quaternary phosphonium polyfluoride trimerization catalyst corresponding to the formula $$R_4P^+F^-n(HF)$$

wherein
  R represents identical or different, optionally branched aliphatic, aromatic and/or araliphatic $C_1$–$C_{20}$ groups, or two or more R groups may also form, with one another and with the phosphorus atom, saturated or unsaturated rings and
  n has a value of 0.1 to 20.

12 Claims, 2 Drawing Sheets

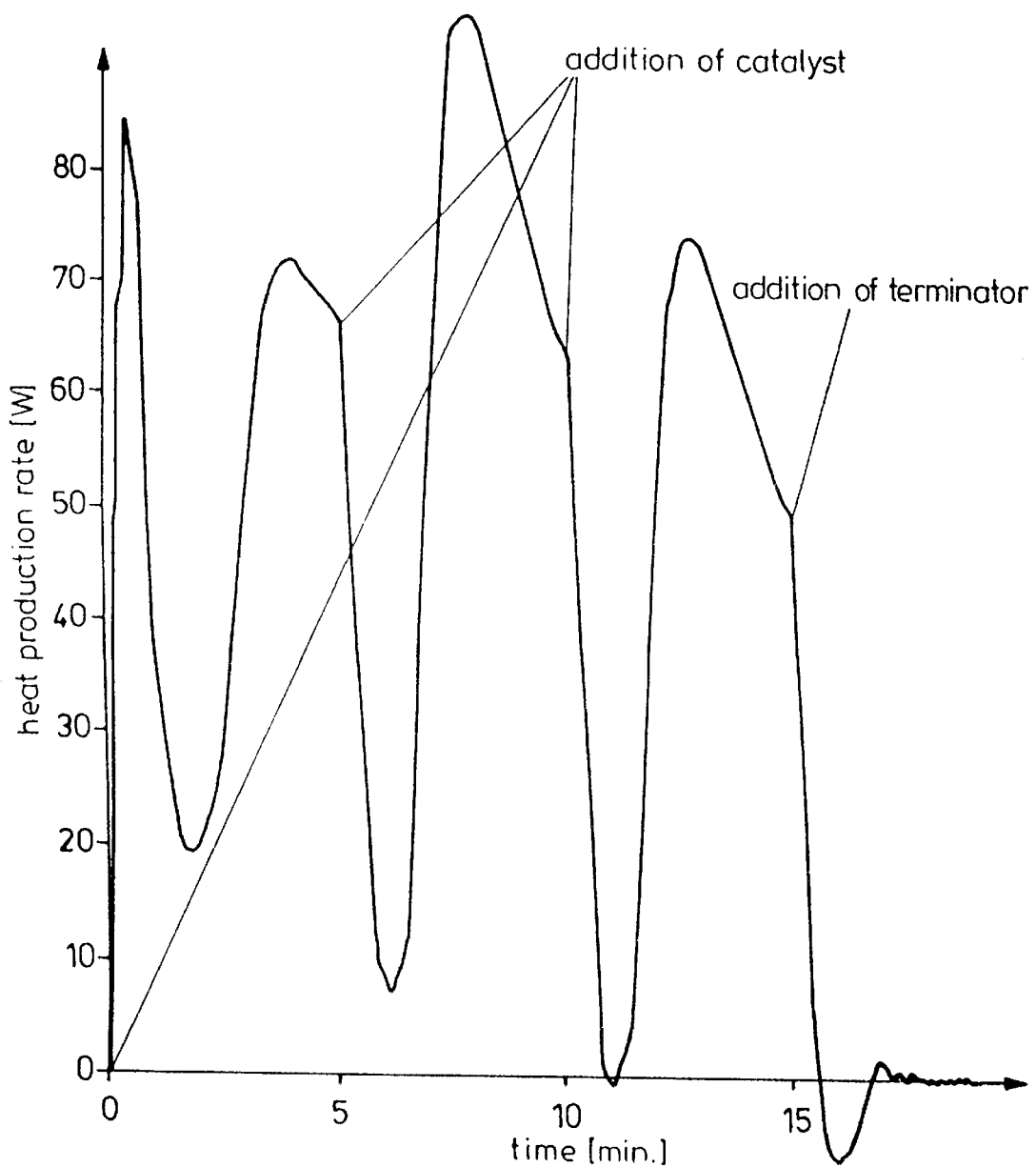
Fig. 1 - Prior Art

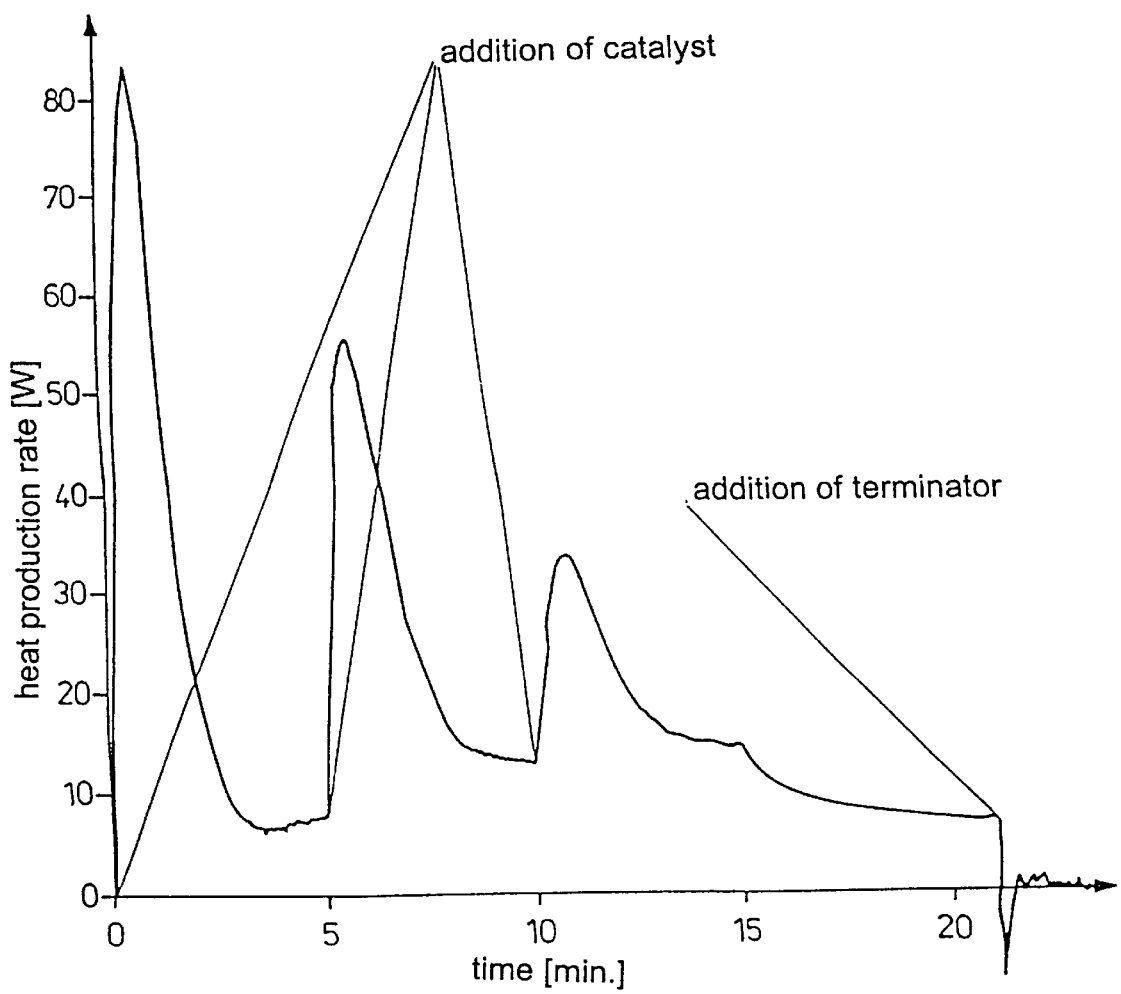

PROCESS FOR PREPARING POLYISOCYANATES CONTAINING IMINOOXADIAZINEDIONE GROUPS

BACKGROUND OF THE INVENTION

1. Field of the Invention

The present invention relates to a process for the preparation of trimerized polyisocyanates that contain iminooxadiazinedione groups in the presence of a quaternary phosphonium polyfluoride trimerization catalyst.

2. Description of the Prior Art

Polyisocyanates containing iminooxadiazinedione groups (asymmetric trimers) are valuable, high quality raw materials, which may be used, e.g., for the manufacture of polyurethane lacquers and coatings (e.g. DE-A 19,611,849). These polyisocyanates are present as a subsidiary component in the well known polyisocyanates containing isocyanurate groups (symmetric trimers).

Isocyanate oligomers having a significantly increased iminooxadiazinedione content are the subject of DE-A 19,611,849. Their advantageous properties, for example, as a raw material for the manufacture of polyurethane lacquers and coatings, are described. For (di)isocyanate oligomers having at least three NCO groups, polyisocyanates containing iminooxadiazinedione groups have the lowest viscosity.

The preparation of isocyanate trimers containing iminooxadiazinedione groups using ammonium polyfluoride catalysts is described in the examples of DE-A 19,611,849. When this process was transferred from laboratory scale to industrial scale, it was found that the proportion of asymmetric trimer in the trimer mixture varied. In this application the term "trimer mixture" is defined as the sum of symmetric trimers (isocyanurates) and asymmetric trimers (iminooxadiazinediones). The products which can be prepared in that manner may occasionally also exhibit a high level of turbidity (greater than 1.5 TE(F) when measured using a device from Hach).

Thermokinetic studies of the trimerization reaction of hexamethylene diisocyanate (HDI) using ammonium polyfluoride catalysts in a reaction calorimeter (for the measuring arrangement and principle see J. Thermal Anal. 1983, 27, 215–228) showed that in some tests the progression of the evolution of heat with time differs greatly from the usual pattern. The general pattern is increased production of heat after addition of the catalyst and then a more or less slow but steady fall in the heat of reaction as a result of deactivation of the catalyst in the reaction mixture, which is caused by thermal decomposition and reaction with trace impurities in the isocyanate starting material.

In contrast, in many cases the expected rapid release of heat of reaction occurred first, after which the reaction rather untypically died down rapidly and then started up again. Surprisingly, the addition of further catalyst did not immediately accelerate the reaction, but rather the reaction slowed down for a short time immediately after addition of the catalyst and then, after passing a minimal heat production rate, accelerated again for no obvious external reason as shown in Example 2 and FIG. 1.

However, this phenomenon is not observed in all cases. Nor is it dependent on the reaction temperature. If no abnormal progression of the heat production curve with time is observed, the proportion of asymmetric trimers is at the same high level achieved in laboratory tests (i.e., over 30 mole % in the trimer mixture). If the above-mentioned abnormal progression of the heat production curve is observed, products having a much lower iminooxadiazinedione content are obtained.

Obviously, in a scarcely foreseeable manner, the actual catalytically active species, which yields different products according to the type of reaction (normal versus abnormal in the sense of the preceding description), forms only during the reaction from the ammonium polyfluoride that is added, as a result of the effect of the isocyanate to be oligomerized or the secondary products present in these isocyanates.

This circumstance renders considerably more difficult the specific, reproducible industrial manufacture of high quality lacquer polyisocyanates having reproducible properties such as viscosity, NCO content, color index, turbidity, etc.

An object of the present invention is to provide a reproducible process which is not subject to the above-mentioned incalculabilities such that 1) it is possible to carry out the reaction in a foreseeable manner in direct dependence on the amount of catalyst used,
2) the heat produced in the exothermic reaction is to occur uniformly and be removable uniformly and
3) it is to be possible to prepare products having an expected, uniform composition and quality.

This object may be achieved by the process according to the invention by catalyzing isocyanate trimerization with quaternary phosphonium polyfluorides.

SUMMARY OF THE INVENTION

The present invention relates to a process for the preparation of trimerized polyisocyanates that contain at least 30 mole % of iminooxadiazinedione groups (asymmetric trimers) in the trimer mixture, by catalytically trimerizing a starting isocyanate selected from organic di- or polyisocyanates having a number average molecular weight of 140 to 600 and containing aliphatically, cycloaliphatically and/or araliphatically bound isocyanate groups in the presence of a quaternary phosphonium polyfluoride trimerization catalyst corresponding to the formula

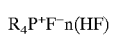

wherein
R represents identical or different, optionally branched aliphatic, aromatic and/or araliphatic $C_1$–$C_{20}$ groups, or two or more R groups may also form, with one another and with the phosphorus atom, saturated or unsaturated rings and
n has a value of 0.1 to 20.

BRIEF DESCRIPTION OF THE DRAWINGS

FIG. 1 represents a graph of heat production vs. time for a prior art trimerization reaction.

FIG. 2 represents a graph of heat production vs. time for an embodiment of the trimerization reaction according to the invention.

DETAILED DESCRIPTION OF THE INVENTION

In accordance with the present invention the term "trimer mixture" includes both isocyanurate and iminooxadiazinedione groups.

Preference is given to the process in which there are used as the isocyanate component to be trimerized aliphatic diisocyanates having a molecular weight of 140 to 300 in the form of pure compounds or mixtures of these compounds. The products of the process preferably contain at least 35%, more preferably at least 40 mole % of iminooxadiazinedione groups (asymmetric trimers) in the trimer mixture.

In accordance with a preferred embodiment of the present invention the quaternary phosphonium polyfluorides trimerization catalysts are used in admixture with alcohols having a molecular weight of 32 to 250 g/mol.

To carry out the process according to the invention the trimerization catalysts may either be used as pure compounds or as mixtures of compounds of the formula $R_4P^+$ $F^-n(HF)$, wherein R represents identical or different, optionally branched, aliphatic, aromatic and/or araliphatic $C_1$–$C_{20}$ groups. The R groups may optionally be substituted. Examples of suitable catalysts include products which are commercially available, optionally in the form of their salts with counterions other than polyfluoride, which can readily be converted into the polyfluoride form, such as chlorides, bromides, iodides and (hydrogen) sulfates. See, for example, Synthesis 1988, 12, 953–955 and Example 1. Examples include tetrakis(hydroxymethyl)phosphonium chloride and sulfate; and tetraethyl-, tetrabutyl-, tetraoctyl-, tetrakis (hexadecyl)-, tributyl(tetradecyl)-, tributyl(hexadecyl)- and trioctyl(octadecyl)-phosphonium chloride, bromide or iodide.

Since the preceding catalysts in their pure form are in most cases solid (see Example 1), catalyst solvents are usually required for their use in the isocyanate trimerization according to the invention. Examples of these solvents include straight-chain and branched, primary, secondary and tertiary alcohols having 1 to 20 carbon atoms, preferably 1 to 8 carbon atoms, such as methanol, ethanol, n- and iso-propanol, 1- and 2- butanol, isobutanol and 2-ethylhexanol.

Triphenyl(alkyl) derivatives may also be used, although they are less preferred due to their poorer solubility in the previously mentioned solvents, especially alcohols, when compared to the purely aliphatically substituted catalysts (Examples 1c and 3–15).

Although the use of polyfluorides is generally known from DE-A 19,611,849, this reference does not disclose the advantages of using quaternary phosphonium polyfluorides to prepare polyisocyanates having an especially high content of iminooxadiazinedione groups in such a manner that the preparation is highly reproducible and the products formed are also free of turbidity under all preparation conditions.

All of the examples of DE-A 19,611,849 relate to catalysis with polyfluorides based on quaternary ammonium salts, which results in the disadvantages previously discussed. The particular role played by the nature of the cation in the catalyst molecule is not discussed.

Based on the teachings of DE-A 19,611,849 it is surprising that the nature of the counterion for the polyfluoride anion (in this case: quaternary phosphonium) has a decided influence on the reproducible progression of the desired reaction and the formation of high quality products having a high iminooxadiazinedione group content and a uniform quality (e.g. low turbidity). The use of optionally immobilized phosphonium fluorides optionally prepared in situ (phase transfer catalysis, see. Isr. J. Chem. 1985, 26, 222–244, however, phosphonium fluorides are not described therein) for isocyanate trimerization is proposed in DE-A 3,902,078, DE-A 3,827,596 and EP-A 0,315,692.

In EP-A 0,315,692, which describes concept of phase transfer catalysis, potassium fluoride-catalyzed processes for the preparation of compounds having isocyanurate groups are described. The simultaneous presence of phosphonium compounds to "increase the efficiency of the reaction" is also proposed. Polyfluorides are not mentioned. Also, phosphonium salts are not used in the examples. The specification primarily relates to the trimerization of aromatic isocyanates (TDI, MDI). The trimerization of isocyanates containing aliphatically bound NCO groups to form isocyanurate groups is only demonstrated by the reaction of n-butyl isocyanate with potassium fluoride in two examples. In Example1 of EP-A 0,315,692 potassium fluoride was used as the sole catalyst; in Example 5 potassium fluoride was used in the presence of a quaternary ammonium salt (benzyltrimethylammonium chloride.

The method is not practical for use on a commercial scale because of the following disadvantages:

1) the high reaction temperature (120° C.) and the comparatively long reaction times (8 hours in Example 1, 4 hours in Example 5 of EP-A 0,315,692) with a high catalyst concentration;
2) the technically disadvantageous removal of the solid potassium salt components after the reaction by filtration (Example 1 of EP-A 0,315,692) or by washing with water, which prevents the preparation of products containing free isocyanate groups (Example 5 of EP-A 0,315,692) and
3) because of the combined of a phosphonium salt and potassium fluoride, fluoride ions are "extracted" continuously from the insoluble, inorganic phase, which is described as the actual catalyst, into the organic isocyanate-containing phase.

EP-A 235,388 describes a process for the preparation of mixed isocyanate-polycarboxylic acid/polycarboxylic acid anhydride secondary products using alkali metal fluorides as catalysts with the simultaneous presence of quaternary onium salts. However, it is stated at page 2, column 2, lines 21–23, that no products are formed from the reaction of the NCO groups with one another. To the contrary in accordance with the present invention these are precisely the products (asymmetric and symmetric trimers) that are made.

With the exception of DE-A 19,611,849, no prior publication describes the advantageous use of polyfluorides, i.e. HF-fluoride adducts, for isocyanate modification. In addition, DE-A 3,902,078 teaches that phosphonium fluorides are "less preferred" than the corresponding ammonium fluorides in several places (page 3, lines 32–33, lines 60–61 and page 4, line 12). It is also mentioned that in the resulting products the "iminooxadiazinedione content remains subordinate" (page 4, lines 51–52). Examples 6 to 9 of DE-A 3,902,078, which describe the proportional formation of iminooxadiazinediones as well as isocyanurate and oxadiazinetrione as the two main products of the reaction, suggests that the formation of iminooxadiazinediones requires the presence of $CO_2$ in the trimerization reaction and refers to this reaction as an undesired subsidiary reaction.

Based on the teachings of the preceding prior art it would not be apparent that quaternary phosphonium polyfluorides which are completely soluble in the organic medium are especially advantageous for the highly reproducible preparation of turbidity-free isocyanate trimer resins having a high content of iminooxadiazinedione groups in the trimer mixture.

Especially surprising is the observation that, in contrast to catalysis using quaternary ammonium polyfluorides, which are chemically very similar, the use according to the invention of quaternary phosphonium (poly)fluorides for isocyanate trimerization produces the "normal" reaction progression in thermokinetic measurements, i.e., the expected pattern of increased heat production after addition of the catalyst and then a slow but steady fall as a result of deactivation of the catalyst in the reaction mixture, for example, by reaction of the catalyst with trace impurities in the starting isocyanate (Example 3-1 and FIG. 2).

These effects are not due to the higher thermal stability of tetraorganylphosphonium salts when compared to the corresponding tetraorganylammonium salts, which is known from the literature (see, for example, Methoden der Organischen Chemie, "Houben-Weyl", 4th edition, G. Thieme Verlag, Stuttgart, Vol. XII/1, p. 47 and ibid., Vol. XI/2, p. 633 ff), as measurements of the isocyanate trimerization at various temperatures prove. In any case, the trimerization reaction preferably takes place at temperatures which do not reveal any signs of decomposition in differential thermal analytical measurements (DTA) either in the case of the ammonium polyfluorides or in the case of the phosphonium polyfluorides.

Obviously, the formation of the actual catalytically active species ("activated complex") from the original catalyst molecule and isocyanate group(s) in the presence of excess starting isocyanate can be fulfilled in a considerably better and, especially, more reproducible manner by the phosphonium catalysis according to the invention instead of the corresponding ammonium compounds.

The value of n in formula (I) is not critical; however, for practical considerations and also because of the unpleasant physiological properties of hydrogen fluoride, it is not used in large molar excesses, based on fluoride ($F^-$) present, even though these excesses are suitable for preparing polyisocyanates having a high iminooxadiazinedione content. Even a catalyst system having a 20 times molar excess of hydrogen fluoride, based on fluoride ($F^-$) present, yields products which are perfect in terms of quality and have a high iminooxadiazinedione content (over 50 mole % in the trimer mixture, Examples 3-11 to 3-13). However, stoichiometric (n=1) or less than stoichiometric amounts of HF (n=e.g. 0.5), based on the amount of fluoride ions, are entirely satisfactory, so that n is preferably 0.1 to 2.5.

The process according to the invention is carried out at a temperature of 20° C. (room temperature) to 200° C., preferably 30° C. to 120° C. and more preferably from 40° C. to 100° C., with proportional reaction of the isocyanate groups of the starting isocyanate. The degree of reaction $R_{NCO}$, which is calculated as the quotient of the difference between the NCO content of the starting isocyanate before trimerization and the NCO content of the reaction mixture after termination of the reaction divided by the NCO content of the starting isocyanate before trimerization, is 5% to 60%, preferably 10% to 40%.

Any unreacted monomer may, after deactivation of the catalyst system, be separated off by any known method, for example, by (thin-layer) distillation or extraction, and then recycled.

To deactivate the catalyst system after the desired $R_{NCO}$ has been reached, any of the known prior art methods for terminating the trimerization reaction with isocyanurate formation may be used. Examples include the addition of less than, equal to or greater than stoichiometric amounts of strong acids or acid derivatives with respect to the molar amount of fluoride (MW 19) used (e.g., benzoyl chloride, phosphorous and phosphoric acid and acid esters thereof, but not HF), adsorptive binding of the catalyst and subsequent removal by filtration and thermal deactivation.

The removal of excess starting (di)isocyanate, provided that it is a low molecular weight "monomeric" (di) isocyanate, is preferably carried out when the products of the process according to the invention are intended for use in the polyurethane lacquer and coating compositions. In this regard the excellent color index and color stability of the products, as well as their high resistance to cleavage to reform the monomeric starting (di)isocyanate, are advantageous.

To prepare the trimers according to the invention, catalyst concentrations (based on the weight of the starting isocyanate and the fluoride ion, MW 19) of 1 ppm to 1%, preferably 1 ppm to 0.1% and more preferably 1 ppm to 0.05%, are sufficient.

According to a continuous embodiment of the process according to the invention, the oligomerization is carried out in a tube reactor. The very low tendency of phosphonium polyfluoride catalysts to form gel particles in the product, even when used in highly concentrated solution or in pure form, is an advantage in this process.

The process according to the invention may be carried out either without a solvent or with dilution of the starting isocyanate. Suitable organic compounds include those that are inert towards NCO groups, such as toluene, xylene(s), higher aromatic compounds, esters, ethers, ketones, $C_{12}$–$C_{20}$-alkylsulfonic acid esters and mixtures thereof.

Suitable starting isocyanates for carrying out the process according to the invention include di- or polyisocyanates having a number average molecular weight of 140 to 600 and containing aliphatically, cyclo-aliphatically and/or araliphatically bound isocyanate groups. The starting isocyanates may be used in pure form or in the form of mixtures. Examples which may be mentioned include hexamethylene diisocyanate (HDI), 2-methylpentane-1,5-diisocyanate (MPDI), 1,3-bis(isocyanatomethyl)-cyclohexane (1,3-$H_6$-XDI), 3(4)-isocyanatomethyl-1-methyl-cyclohexyl isocyanate (IMCI); isophorone diisocyanate (IPDI), bis(isocyanatomethyl)-norbornane (NBDI), 4-isocyanatomethyl-1,8-octane diisocyanate (triisocyanatononane, TIN), 1,3-bis(isocyanatomethyl)-benzene, 1,3-bis(2-isocyanatopropyl-2)benzene and bis(4(2)-isocyanatocyclohexyl)methane ($H_{12}$MDI, Desmodur W, available from Bayer AG). The process used for preparing the starting isocyanates, i.e., with or without the use of phosgene, is not important. Preferred starting isocyanates are HDI, MPDI, 1,3-$H_6$XDI, NBDI and mixtures of HDI and IPDI.

In certain instances it is advantageous to use mixtures of starting isocyanates in the process according to the invention, for example, in order to satisfy the property requirements for the product. For example, in the (initial) coating of motor vehicles, polyisocyanate mixtures based on optionally branched, linear-aliphatic diisocyanates such as HDI and cycloaliphatic diisocyanates such as IPDI or $H_{12}$MDI are used. These mixtures are generally prepared by the mixing polyisocyanates that have been separately prepared from the two types of starting diisocyanates. However, it may be advantageous to prepare them by simultaneous mixed trimerization from the corresponding mixture of the monomeric components (EP-A 0,047,452).

Many polyisocyanates based on the known cycloaliphatic diisocyanates are solid. They occasionally have such a high melt viscosity that separation of the monomers by (thin-layer) distillation presents considerable difficulties. For that reason, solvents or flow additives must be used during their processing and sometimes occasionally, also for thin-layer distillation. If too great a loss in the degree of reaction (resin yield) and NCO functionality in the preparation of these polyisocyanates is not acceptable, the resulting isocyanurate polyisocyanates based on cycloaliphatic diisocyanates have solution concentrations of about 70% resin solids and readily processable dynamic viscosities of 1 to 10 Pa·s (23° C.).

To the contrary if mixtures of linear aliphatic isocyanates, such as HDI, and cycloaliphatic diisocyanates, such as IPDI, are trimerized by the process according to the invention with at least partial iminooxadiazine-dione formation, products which are capable of flowing at room temperature (viscosity at 23° C. less than 100 Pa·s) are obtained. These products also exhibit a drastically more rapid fall in viscosity upon the addition of solvents than do prior art products prepared from the same isocyanate starting material and having the same NCO functionality and average molecular weight as shown by Example 4.

Accordingly, the products and product mixtures obtained by the process according to the invention are suitable starting materials for a variety of uses, including the manufacture of optionally foamed plastics as well as lacquers, coating compositions, adhesives and additives.

Before they are used as the isocyanate component in polyurethane systems, the products of the present invention may optionally be modified by reacting the isocyanate groups to incorporate urethane, urea, biuret and/or allophanate groups or by reacting some or all of the NCO groups with reversible blocking agents. Suitable blocking agents include phenols, lactams such as $\epsilon$-caprolactam, oximes, di- and triazoles, amines such as diisopropylamine and CH-acid compounds such as malonic acid dialkyl esters and acetoacetic ester.

The products prepared according to the invention, optionally in blocked form, are especially suitable for the manufacture of optionally water-dispersible one- and two-component polyurethane coating compositions because their solution and melt viscosities are reduced when compared to isocyanurate-polyisocyanates, while their properties profile is equally high or is improved. Therefore, the HDI-based products of the invention are more stable towards the occurrence of flocculation or turbidity, even when highly diluted in lacquer solvents, when compared to the known corresponding products containing mainly isocyanurate groups. Their resistance towards the effects of moisture (e.g., the formation of a skin in open packaging or the matt appearance of surfaces lacquered at high humidity and a high ambient temperature, so-called "downglossing") is also improved when compared with products containing isocyanurate groups.

The invention is further illustrated but is not intended to be limited by the following examples in which all parts and percentages are by weight unless otherwise specified.

EXAMPLES

Mole percents were determined by NMR spectroscopy and always, unless indicated otherwise, were based on the sum of the NCO secondary products formed as a result of the modification reaction ("trimerization"). Measurements were carried out using a DPX 400 device from Bruker on approximately 5% ($^1$H-NMR) or approximately 50% ($^{13}$C-NMR) samples in dry CDCl$_3$ at a frequency of 400 MHz ($^1$H-NMR) or 100 MHz ($^{13}$C-NMR). As reference for the ppm scale there were chosen small amounts of tetramethylsilane in the solvent with a $^1$H chemical shift of 0 ppm ($^1$H-NMR) or the solvent itself (CDCl$_3$) with a shift of 77.0 ppm ($^{13}$C-NMR). Data for the chemical shift of the compounds in question has been taken from the literature (see Die Angewandte Makromolekulare Chemie 1986, 141, 173–183 and literature cited therein) or obtained by measurement of model substances. 3,5-dimethyl-2-methylimino-4,6-diketo-1,3,5-oxadiazine, which was obtained from methyl isocyanate in a yield of approximately 70% following the process described in Ber. d. dtsch. Chem. Ges. 1927, 60, 295, using approximately 3% tri-n-butylphosphine as catalyst, had the following NMR chemical shifts (in ppm): 3.09; 3.08 and 2.84 ($^1$H-NMR, CH$_3$) or 148.3; 144.6 and 137.3 ($^{13}$C-NMR, C=O/C=N). The products of the process having an iminooxadiazinedione structure have very similar $^{13}$C-NMR chemical shifts of the C=O/C=N atoms and can beyond doubt be distinguished as such from other isocyanate secondary products.

Dynamic viscosities were determined at 23° C. using a VT 550 viscosimeter from Haake. By means of measurements at different shear rates it has been ensured that the flow properties of the described polyisocyanate mixtures according to the invention, as well as those of the comparison products, correspond to those of ideal Newtonian fluids. It was therefore unnecessary to indicate the shear rate.

Residual monomer contents were determined by gas chromatography.

The turbidity of the trimer resins was determined using a device from Hach. To that end, scattered light measurements were carried out at 90° to the direction of a light beam having a wavelength of from 400 to 800 nm guided through the resin sample, and were given in units based on formazine standard solutions, TE(F).

The majority of the reactions were carried out using HDI as the isocyanate to be trimerized and catalysts based on tetrabutylphosphonium hydrogen difluoride under a nitrogen atmosphere. This was merely to demonstrate the advantages of the process according to the invention and was not intended to constitute any limitation of the present invention to the systems or reaction conditions described.

Example 1

Preparation of Quaternary Phosphonium Polyfluorides (Stock Solutions)

The solutions were prepared following the procedure proposed in J. Org. Chem. 1989, 54, 4827–4829 for the preparation of similar ammonium compounds.

a) Bu$_4$P$^+$F$^-$ n HF in methanol/isopropanol 953.8 g of a 71.4% Bu$_4$P$^+$Cl$^-$ solution in isopropanol (Cyphos 443P, product from Cytec), which corresponds to 2.3 moles of Bu$_4$P$^+$Cl$^-$, were dissolved in 1 kg of commercial methanol (approximately 0.2% H$_2$O); 150 g (2.58 moles) of powdered potassium fluoride were added thereto, and stirring was carried out for 24 hours at 20–25° C. (room temperature). The mixture was then filtered and the filtration residue was washed with 2×100 g of commercial methanol; a further 150 g (2.58 moles) of powdered potassium fluoride were added to the combined filtrates, and stirring was carried out for 24 hours at 20–25° C. (room temperature). After subsequent filtration and washing again with 2×100 g of commercial methanol, the mixture was largely freed of excess methanol and isopropanol in a rotary evaporator at a maximum temperature of 30° C. and a pressure of approximately 1 mbar, and filtration was carried out again. The virtually colorless solution obtained had the following properties:

fluoride (with ion-sensitive electrode at pH 5.5): 5.0%
chlorine (total, after decomposition, gravimetric): 0.4%
MeOH (gas-chromatographic, after standardization): 16.3%
i-PrOH (gas-chromatographic, after standardization): 7.3%

5.27 g of anhydrous HF were added in portions to 100 g of the preceding solution with stirring and while cooling (<20° C.). When the exothermic reaction had subsided, the tetrabutylphosphonium hydrogen difluoride solution so obtained (stock solution 1, calculated fluoride content, F⁻, not total fluorine: 4.75%) was used for the trimerization in Example 3–1.

Over a period of 6 hours in a rotary evaporator, at a maximum temperature of 30° C. and a pressure of approximately 1 mbar, a portion of stock solution 1 (200 g) was freed from methanol and isopropanol, to constant weight, to an even greater extent than was possible in the fluoride form under those conditions (pressure, temperature). A colorless solution (166 g) having the following properties was obtained:

fluoride (with ion-sensitive electrode at pH 5.5; under those conditions both the fluorine originally present as F⁻ and the fluorine added as HF were detected as fluoride, F⁻): 10.8%

HF content (simple acidimetric titration with 0.1 n NaOH against phenolphthalein): 5.7% from the preceding two values a (formal) F⁻ content of the solution of 5.4% and a molar F:HF ratio of approximately 1:1 were calculated, i.e. no HF was removed as a result of further concentration in vacuo chlorine (total, after decomposition, gravimetric): 0.50%

MeOH (gas-chromatographic, after standardization): 3.4% i-PrOH (gas-chromatographic, after standardization): 2.1% viscosity at 23° C. (mPa·s): 280

The mixture was liquid at room temperature and solidified to a white crystal-line composition only when stored in a deep freeze (−12° C.). The composition became virtually completely liquid again even when subsequently stored in a refrigerator (−2° C.) (turbid solution containing solids particles). Subsequent storage at room temperature (20–25° C.) again yielded a homogeneous, clear, colorless solution having the above-mentioned analytical data.

The highly concentrated solution so obtained (hereinafter stock solution 2) was used for HDI trimerization as such (Example 3-0) as well as in admixture with various alcohols, with further HF or with further phosphonium fluoride (see Example 3, Table 1).

b) $Bu_3(C_{14}H_{29})P^+F^-$ in methanol/isopropanol 500 g of a 74.2% $Bu_3(C_{14}H_{29})P^+F^-$ solution in isopropanol (Cyphos 3453P, product from Cytec), which corresponded to 0.85 moles of $Bu_3(C_{14}H_{29})P^+Cl^-$, were dissolved in 0.5 kg of commercial methanol (approximately 0.2% $H_2O$); 50 g (0.86 moles) of powdered potassium fluoride were added thereto, and stirring was carried out for 24 hours at 20–25° C. (room temperature). The mixture was then filtered and the filtration residue was washed with 2×50 g of commercial methanol; a further 50 g (0.86 moles) of powdered potassium fluoride was added to the combined filtrates, and stirring was carried out for 24 hours at 20–25° C. (room temperature). After subsequent filtration and washing again with 2×50 g of commercial methanol, the mixture was largely freed of excess methanol and isopropanol in a rotary evaporator at a maximum temperature of 30° C. and a pressure of approximately 1 mbar, and filtration was carried out again. The resulting solution had the following properties:

fluoride (with ion-sensitive electrode at pH 5.5): 3.65%
chlorine (total, after decomposition, gravimetric): 0.145%

MeOH (gas-chromatographic, after standardization): 9.1% i-PrOH (gas-chromatographic, after standardization): 3.8% c) $Ph_3(Bu)P^+F^-$ in methanol 20 g (56.3 mmoles) of $Ph_3(Bu)P^+Cl^-$ (product of Chemconserve) were dissolved in 40 g of commercial methanol (approximately 0.2% $H_2O$). 3.3 g (56.8 mmoles) of powdered potassium fluoride were added thereto, and stirring was carried out for 24 hours at 20–25° C. (room temperature). The mixture was then filtered and the filtration residue was washed with 2×5 g of commercial methanol; a further 3.3 g (56.8 mmoles) of powdered potassium fluoride were added to the combined filtrates, and stirring was carried out for 24 hours at 20–25° C. (room temperature). After subsequent filtration and washing again with 2×5 g of commercial methanol, the mixture was largely freed of excess methanol in a rotary evaporator at a maximum temperature of 30° C. and a pressure of approximately 1 mbar until crystallization began, and filtration was carried out again. During the filtration care was taken to ensure that only potassium salts which formed as a result of further concentration of the solution were separated off and no phosphonium salt remained in the filtration residue (solubility sample).

The resulting solution had the following properties:
fluoride (with ion-sensitive electrode at pH 5.5): 3.15%
chlorine (total, after decomposition, gravimetric): <0.2%
MeOH (gas-chromatographic, after standardization): 42.8%

Analogously to the preparation of stock solution 1 from the intermediate tetrabutylphosphonium fluoride solution, the quaternary phosphonium fluorides obtained in Examples 1b) and 1c) were converted into the corresponding hydrogen fluorides by the addition of one equivalent of HF and were used in the manner described in Example 3 for HDI trimerizations (tests 3-14 and 3-15).

Example 2 Comparison Example

HDI trimerization using a quaternary ammonium hydrogen difluoride catalyst 1 (DE-A 19,611,849 or U.S. Pat. No. 5,914,383).

The catalyst was prepared according to J. Org. Chem. 1989, 54, 4827–4829 by anion exchange from aliquat 336 (quaternary ammonium chloride $R_3(Me)N^+Cl^-$, $R=C_8-C_{10}$-alkyl, $C_8$ was predominant, from Fluka AG, the product contained isopropanol) with KF in MeOH, and was converted into the $R_3(Me)N^+[HF_2]^-$ form by the subsequent addition of HF, as described in Example 1 (F⁻ content of the solution: 2.05%, not total fluorine from $HF_2^-$).

In a V4A reactor as described in J. Thermal Anal. 1983, 27, 215–228, 320 g (1.9 moles) of HDI were first freed of dissolved gases by stirring under vacuum (0.1 mbar) for approximately one hour at 60° C. and a stirrer speed of 1200 min⁻¹. Aeration with nitrogen was carried out, and then 26 ppm of catalyst 1 (based on fluoride ion, MW 19, and HDI used), were added (first addition of catalyst in FIG. 1). After 5 minutes and again after a further 5 minutes, an amount of catalyst corresponding to 6 or 3 ppm of F⁻, respectively, was added (second and third additions of catalyst in FIG. 1). After a total of 15 minutes, the reaction was terminated by the addition of 150 mg of dibutyl phosphate and the reaction mixture was analyzed. The proportion of iminooxadiazinedione in the trimer mixture was 9.5 mole %. The trimer resin obtained after thin-layer distillation using a laboratory thin-layer evaporator, of the short-path evaporator type, at 140°/0.2 mbar had the same low iminooxadiazinedione content and exhibited relatively high turbidity (10.2 TE(F)).

during the reaction. The iminooxadiazinedione contents of the products are set forth in Table 1.

TABLE 1

Results of phosphonium polyfluoride-catalyzed HDI trimerizations

| Exam. no. | Alcohol* | Concentration of $Bu_4P^+F^-$ or $R_4P^+F^-$ [%] (rounded) | $F^-$:HF in the catalyst (molar) | Turbidity of the resin [TE(F)] | Proportion of iminooxadiazine-dione in the trimer mixture [mole %] |
|---|---|---|---|---|---|
| 3-0 | MeOH/iPrOH | 80 | 1:1 | 0.8 | 51 |
| 3-1 | MeOH/iPrOH | 70 | 1:1 | 0.4 | 48 |
| 3-2 | MeOH | 50 | 1:1 | 0.5 | 45 |
| 3-3 | MeOH | 40 | 1:1 | 1.4 | 42 |
| 3-4 | MeOH | 40 | 1:0.5 | 0.8 | 43 |
| 3-5 | iPrOH | 50 | 1:1 | 0.5 | 47 |
| 3-6 | iPrOH | 40 | 1:1 | 0.4 | 42 |
| 3-7 | iPrOH | 30 | 1:1 | 0.6 | 41 |
| 3-8 | iPrOH | 20 | 1:1 | 0.9 | 35 |
| 3-9 | nBuOH | 50 | 1:1 | 0.5 | 44 |
| 3-10 | nBuOH | 30 | 1:0.5 | 0.5 | 38 |
| 3-11 | MeOH/iPrOH | 62 | 1:5 | 0.5 | 53 |
| 3-12 | MeOH/iPrOH | 50 | 1:10 | 0.4 | 59 |
| 3-13 | MeOH/iPrOH | 37 | 1:20 | 0.6 | 64 |
| 3-14 | MeOH/iPrOH | approx. 83% $Bu_3(C_{14}H_{29})P^+[HF_2]^-$ | 1:1 | 0.6 | 43 |
| 3-15 | MeOH | approx. 57% $Ph_3BuP^+[HF_2]^-$ | 1:1 | 0.5 | 44 |

*in Examples 3-2 to 3-10, only the alcohol added for the purpose of further diluting the polyfluoride stock solution 2 is set forth (further explanations see text of Example 3)

Attempts to reproduce those results led to varying, mostly similarly unsatisfactory results.

Example 3

Catalysis with Phosphonium Polyfluorides in Accordance with the Invention

Stock solution 1, as described in Example 1a, was used in a thermokinetic reactor for HDI trimerization (Example 3-1 in Table 1; see also FIG. 2). $R_{NCO}$ was approximately 20%; the reaction was terminated by the addition of a molar amount of dibutyl phosphate, which corresponded to the $F^-$ consumption. The $F^-$ requirement of the reaction at 1st/2nd/3rd additions of catalyst is shown in FIG. 2, i.e., 40/20/11 ppm of $F^-$, based on the weight of HDI and the fluoride ion $F^-$ (MW 19, not total fluorine).

The remaining examples set forth in Table 1 used stock solution 2 (test 3–0), optionally with the addition of alcohols (tests 3-2 to 3-10), HF or tetrabutyl-phosphonium fluoride solution, as catalysts for HDI trimerization. In each case 200 g (1.19 moles) of HDI in a 250 ml four-necked flask having an internal thermometer, a stirrer, a reflux condenser, a gas inlet pipe and a metering device for the catalyst solution were first freed of gases dissolved in the diisocyanate mixture at 60° C. and a pressure of approximately 0.1 mbar for one hour. Aeration with nitrogen was then carried out and the mixture was trimerized while a slight stream of nitrogen was passed through at an internal temperature of 60° C. by the addition of catalyst in portions. The $R_{NCO}$ was in each case approximately 20%, the reaction was terminated by the addition of a molar amount of dibutyl phosphate corresponding to the $F^-$ consumption, not total fluorine. The $F^-$ requirement of the reaction was 10 to 30 ppm $F^-$, based on the weight of HDI used and the fluoride ion ($F^-$, MW 19, not total fluorine). Even when the highly concentrated stock solution 2 was used, no formation of solids was observed

Example 4

HDI/IPDI mixed Trimerization According to the Invention

In a 250 ml, four-necked flask having an internal thermometer, a stirrer, a reflux condenser, a gas inlet pipe and a metering device for the catalyst solution, a mixture of 100 g (0.59 moles) of HDI and 100 g (0.45 moles) of isophorone diisocyanate (IPDI) was first freed of gases dissolved in the diisocyanate mixture for one hour at room temperature and a pressure of approximately 0.1 mbar. The mixture was then heated to an internal temperature of 60° C. while a slight stream of nitrogen was passed through. Then, at that temperature, a total amount of stock solution 1 corresponding to 87 ppm of $F^-$ was added dropwise in portions for approximately 20 minutes such that the internal temperature did not exceed 70° C. Trimerization was carried out until the NCO content of the mixture was 34.0%. The reaction was terminated by the addition of 150 mg of di-n-butyl phosphate and stirring was continued for a further hour at 70° C. Unreacted monomeric diisocyanates were then separated by thin-layer distillation in a short-path evaporator at 0.15 mbar and a heating medium temperature of 180° C. The clear (turbidity=0.9 TE(F)) and virtually colorless resin obtained (66 g, corresponding to a yield of 33%) had in pure form a viscosity of 23,800 mPa·s, an NCO content of 20.2% and residual monomer contents of 0.03% HDI and 0.11% IPDI. The molar ratio of iminooxadiazinediones to isocyanurates was approximately 45:55.

Example 5

Trimerization of $H_6$-XDI According to the Invention 100 g (0.51 moles) of 1,3-bis(isocyanatomethyl) cyclohexane ($H_6$-XDI, Aldrich) were first pretreated as described in Example 4 and then trimerized to an NCO content of 36.4% by the addition, in portions, of stock solution 1 (42 ppm of F⁻ in total) at 58–60° C. over a period of 3 hours. The reaction was terminated by the addition of 100 mg of di-n-octyl phosphate and stirring was carried out for a further hour at 60° C. Unreacted 1,3-bis(isocyanatomethyl)cyclohexane was separated by thin-layer distillation in a short-path evaporator at 0.15 mbar and a heating medium temperature of 150° C. The clear and virtually colorless resin obtained (34 g, corresponding to a yield of 34%) had an NCO content of 19.7% and in pure form was just capable of flowing at room temperature (20–25° C.). The viscosity of an 80% solution in n-butyl acetate was 1570 mPa·s and the NCO content was 15.8%. The residual monomer content was 0.03% 1,3-bis(isocyanatomethyl)-cyclohexane ($H_6$-XDI) and the iminooxadiazinedione content in the trimer mixture was 52%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims

What is claimed is:

1. A process for the preparation of a trimerized polyisocyanate that contains at least 30 mole % of iminooxadiazinedione groups (asymmetric trimers) in the trimer mixture which comprises catalytically trimerizing a starting isocyanate comprising a member selected from the group consisting of organic di- and polyisocyanates having a number average molecular weight of 140 to 600 and containing aliphatically, cycloaliphatically and/or araliphatically bound isocyanate groups in the presence of a quaternary phosphonium polyfluoride trimerization catalyst corresponding to the formula $R_4P^+F^-n(HF)$ wherein R represents identical or different, optionally branched aliphatic, aromatic and/or araliphatic $C_1$–$C_{20}$ groups, or two or more R groups optionally form, with one another and with the phosphorus atom, saturated or unsaturated rings and n has a value of 0.1 to 20.

2. The process of claim 1 wherein the starting isocyanate comprises an aliphatic diisocyanate having a molecular weight of 140 to 300.

3. The process of claim 1 wherein the starting isocyanate comprises hexamethylene diisocyanate (HDI), 1,3-bis(isocyanatomethyl)-cyclohexane ($H_6$-XDI), bis(isocyanatomethyl)norbornane (NBDI), or mixtures thereof.

4. The process of claim 1 wherein the polyisocyanate trimer mixture contains at least 35 mole % of iminooxadiazinedione groups (asymmetric trimers) in the trimer mixture.

5. The process of claim 2 wherein the polyisocyanate trimer mixture contains at least 35 mole % of iminooxadiazinedione groups (asymmetric trimers) in the trimer mixture.

6. The process of claim 3 wherein the polyisocyanate trimer mixture contains at least 35 mole % of iminooxadiazinedione groups (asymmetric trimers) in the trimer mixture.

7. The process of claim 1 wherein said trimerization catalyst is present in admixture with an alcohol having a number average molecular weight of 32 to 250 and the concentration of said trimerization catalyst in the mixture is not less than 10 wt. %.

8. The process of claim 2 wherein said trimerization catalyst is present in admixture with an alcohol having a number average molecular weight of 32 to 250 and the concentration of said trimerization catalyst in the mixture is not less than 10 wt. %.

9. The process of claim 3 wherein said trimerization catalyst is present in admixture with an alcohol having a number average molecular weight of 32 to 250 and the concentration of said trimerization catalyst in the mixture is not less than 10 wt. %.

10. The process of claim 4 wherein said trimerization catalyst is present in admixture with an alcohol having a number average molecular weight of 32 to 250 and the concentration of said trimerization catalyst in the mixture is not less than 10 wt. %.

11. The process of claim 5 wherein said trimerization catalyst is present in admixture with an alcohol having a number average molecular weight of 32 to 250 and the concentration of said trimerization catalyst in the mixture is not less than 10 wt. %.

12. The process of claim 6 wherein said trimerization catalyst is present in admixture with an alcohol having a number average molecular weight of 32 to 250 and the concentration of said trimerization catalyst in the mixture is not less than 10 wt. %.

* * * * *